(12) United States Patent
Burke et al.

(10) Patent No.: US 6,664,427 B1
(45) Date of Patent: Dec. 16, 2003

(54) PROCESS FOR PREPARING ALDEHYDE COMPOUNDS

(75) Inventors: Patrick M. Burke, Wilmington, DE (US); James Michael Garner, Wilmington, DE (US); Wilson Tam, Boothwyn, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/230,465

(22) Filed: Aug. 29, 2002

(51) Int. Cl.[7] .............................. C07C 45/50; C07F 9/02
(52) U.S. Cl. ..................... 568/454; 568/14; 568/15; 568/17
(58) Field of Search ........................... 568/454, 14, 15, 568/17

(56) References Cited

U.S. PATENT DOCUMENTS

| | | | |
|---|---|---|---|
| 4,769,498 A | | 9/1988 | Billig et al. |
| 5,004,823 A | * | 4/1991 | Devon et al. |
| 5,698,745 A | * | 12/1997 | Burke et al. |
| 5,710,344 A | * | 1/1998 | Breikss et al. |

\* cited by examiner

*Primary Examiner*—Johann Richter
*Assistant Examiner*—Sikarl A. Witherspoon

(57) ABSTRACT

The invention relates to a process for the making organic aldehyde compounds from an unsaturated compound by hydroformylation and in the presence of a catalyst system comprising a Group VIII metal and a bidentate phosphorus ligand having two trivalent phosphorus atoms bound to salicylanilide groups.

11 Claims, No Drawings

PROCESS FOR PREPARING ALDEHYDE COMPOUNDS

FIELD OF THE INVENTION

The invention relates to a process for making organic aldehyde compounds from an unsaturated compounds by hydroformylation and in the presence of a catalyst system comprising a Group VIII metal and a bidentate phosphorus ligand having two trivalent phosphorus atoms bound to salicylanilide groups.

BACKGROUND OF THE INVENTION

Ligands that have trivalent phosphorus atoms are characterized in that each trivalent phosphorus atom is bonded with three organic groups. Phosphorus amide compounds are characterized in that the phosphorus atom is linked to the organic group with at least one P—N bond and one or two P-0 bonds (also known respectively as phosphorodiamidites and phosphoramidites). Bidentate phosphorus ligands are furthermore characterized in that two phosphorus atoms are present in the molecule and that one organic bridging group (Q) links both phosphorus atoms. The other organic groups bonded to a single phosphorus atom are often called termini groups (R).

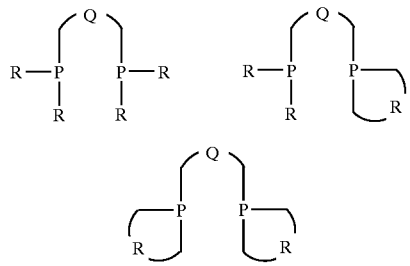

Numerous patents (U.S. Pat. No. 4,769,498, etc.) and other literature describe olefin hydroformylation processes in which an active homogeneous hydroformylation catalyst system is formed by combining rhodium with an organic bidentate phosphite ligand containing two phosphorus atoms linked with an organic dihydroxyl bridging group. The termini groups in these phosphite ligands are most commonly substituted phenol or organic dihydroxyl groups similar to the bridging groups.

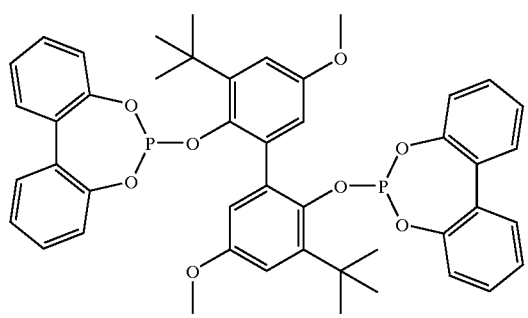

Bidentate Phosphite Ligand

Fewer examples of organic bidentate phosphoramidite ligands have been discovered for olefin hydroformylation with rhodium (WO 9616923, U.S. Pat. No. 5,710,344, etc.). Phosphoramidite ligand examples includes those drawn below.

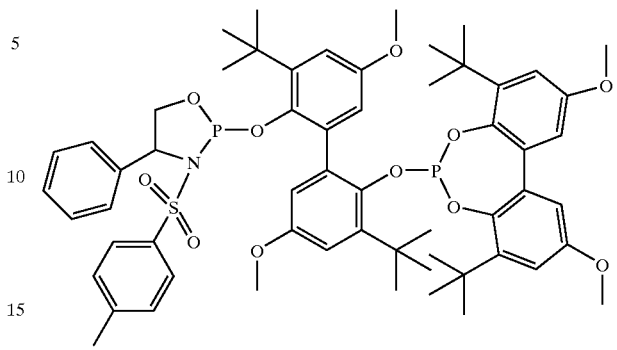

Bidentate Phosphoramidate-Phosphite

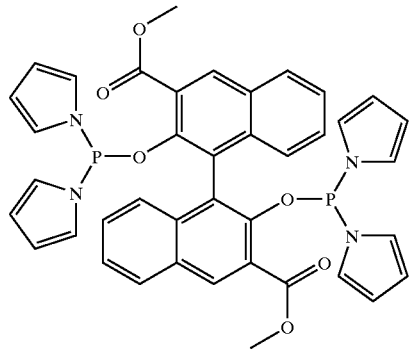

Bidentate Phosphorodiamidiate

However, no prior art has been found that describes an homogeneous rhodium catalyst system for olefin hydroformylation using an organic bidentate phosphite or phosphoramidite ligand comprised of two phosphorus atoms linked by an organic dihydroxyl bridging group with salicylanilide termini groups. Salicylanilides are resonance hybrids of the following two structures.

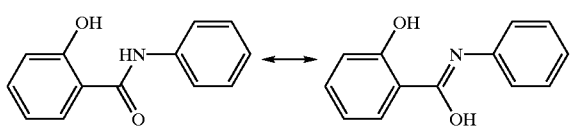

SUMMARY OF THE INVENTION

Disclosed herein is a hydroformylation process for preparing an organic aldehyde compound from an unsaturated organic compound, said method comprising: contacting an unsaturated organic compound with carbon monoxide, hydrogen gas, and a catalyst system, said catalyst system comprising a Group VIII metal, and at least one or a combination of at least two bidentate organic ligands having two trivalent phosphorus atoms, said ligand selected from the group consisting of structure I, II, III, IV, V, and VI:

Structure I
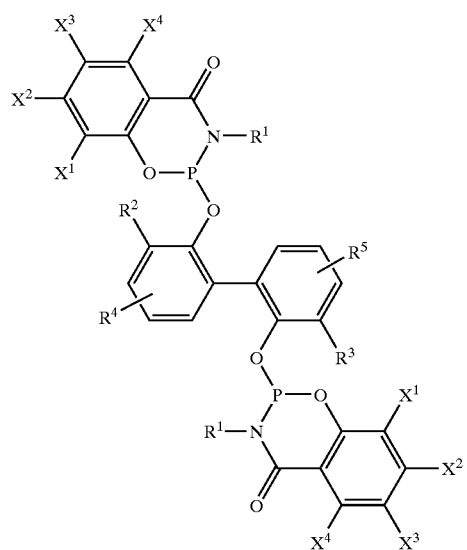
Structure II
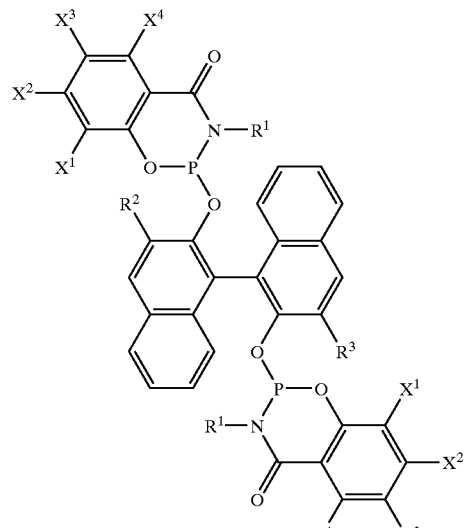
Structure III
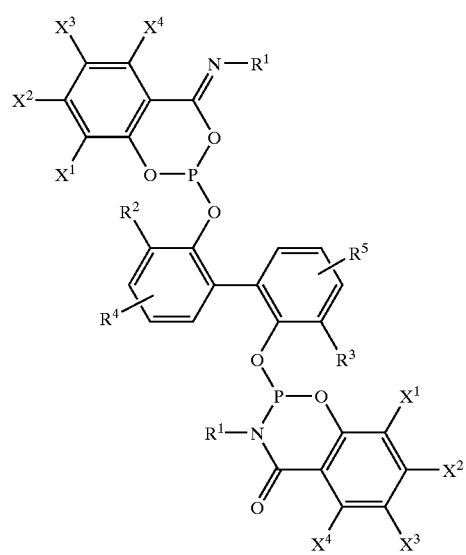
Structure IV
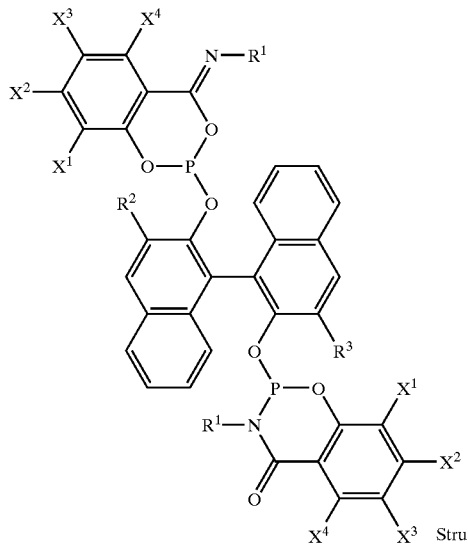
Structure V
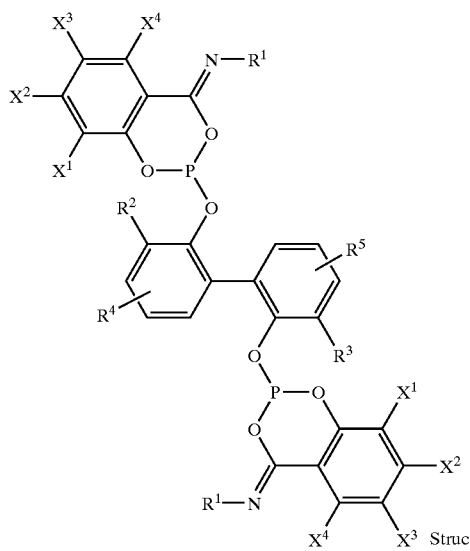
Structure VI
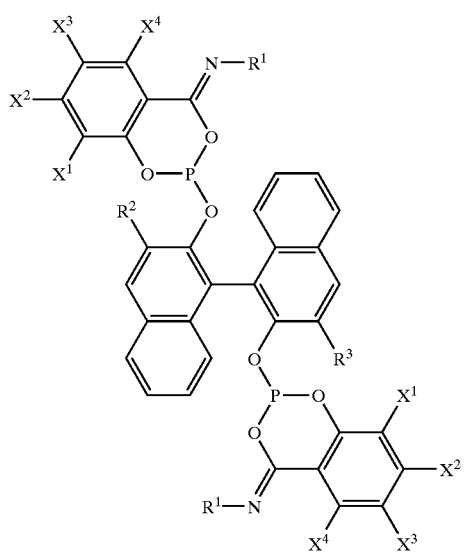

where $X^1$–$X^4$ are C1–C6 alkyl, alkoxy, aryloxy, $NR^6R^7$, Cl, F, or $CF_3$; $R^1$ is independently selected from the group consisting of substituted aryl, phenyl, or fused aromatic ring systems; $R^2$ and $R^3$ are independently selected from the group consisting of hydrogen, alkyl, aryl, triarylsilyl, trialkylsilyl, carboalkoxy, carboaryloxy, aryloxy, alkoxy, alkylcarbonyl, arylcarbonyl, or nitrile; $R^4$ and $R^5$ are independently selected from the group consisting of hydrogen, alkyl, alkoxy; $R^6$ and $R^7$ are independently chosen from alkyl and aryl.

Also disclosed are the novel bidentate ligand compositions having two trivalent phosphorus atoms represented by Structures I through VI above.

DETAILED DESCRIPTION OF THE INVENTION

The present invention provides a hydroformylation process for preparing organic aldehydes using high performing catalyst systems (i.e., selectivity and/or activity) and novel bidentate ligands. A hydroformylation process is used to make the aldehyde from an ethylenically unsaturated compound in the presence of catalyst system that comprises a Group VIII metal or a compound comprising a Group VIII metal, a bidentate ligand having two trivalent phosphorous atoms. When the process according the present invention is used, high selectivities to aldehydes are achieved, combined with a relatively high catalyst activity.

The advantages of this process are even more pronounced when starting from internally unsaturated organic compounds. In comparison to terminal olefins, preparing aldehydes starting from internally unsaturated compounds using previously known hydroformylation processes generally results in lower selectivity to the aldehydes, more hydrogenation of the olefinic double bond and/or lower catalytic activity. An additional advantage of the process according to this invention is that the linearity [linear aldehydes/(linear+branched aldehydes)] is higher.

This object of the present invention is achieved by using at least one ligand of the following formula in a Group VIII metal-catalyzed hydroformylation process:

Structure I

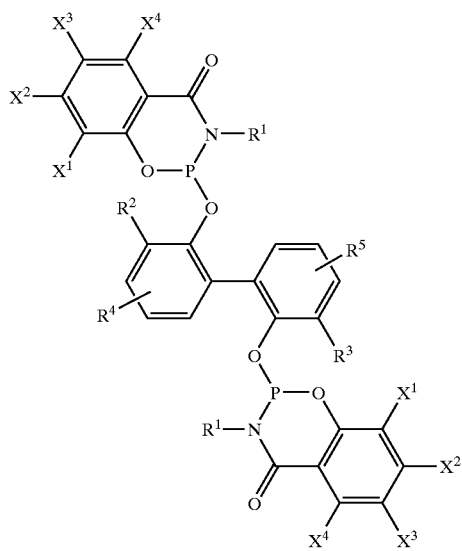

Structure II

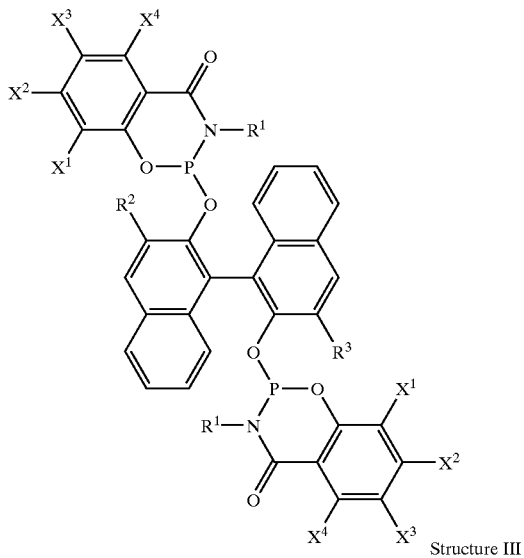

Structure III

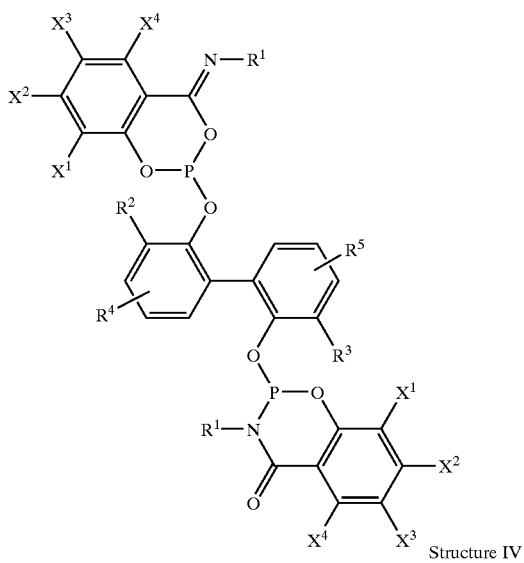

Structure IV

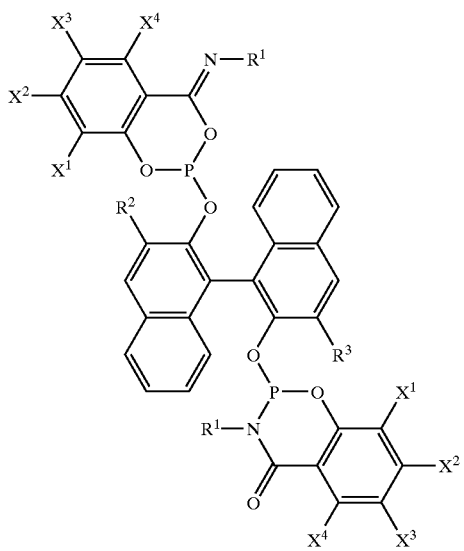

Structure V

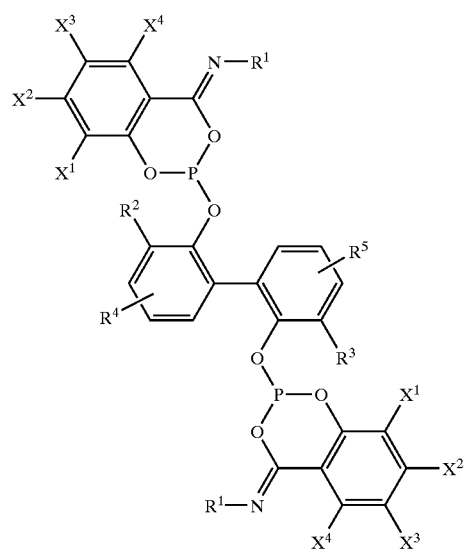

Structure VI

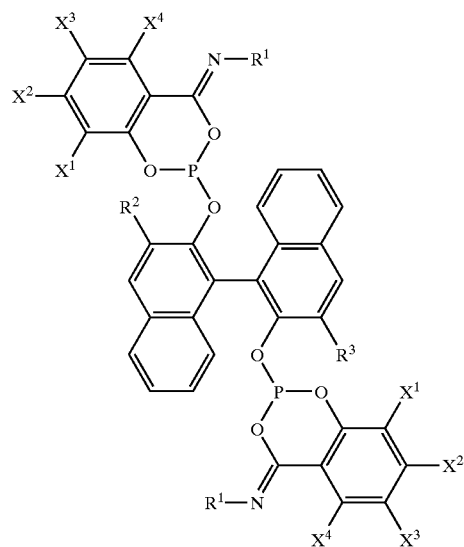

where $X^1$–$X^4$ are C1–C6 alkyl, alkoxy, aryloxy, $NR^6R^7$, Cl, F, or $CF_3$;

$R^1$ is selected from the group consisting of substituted aryl, phenyl, or fused aromatic ring systems;

$R^2$ and $R^3$ each are independently selected from the group consisting of hydrogen, alkyl, aryl, triarylsilyl, trialkylsilyl, carboalkoxy, carboaryloxy, aryloxy, alkoxy, alkylcarbonyl, arylcarbonyl, or nitrile;

$R^4$ and $R^5$ are independently chosen from the group of hydrogen, alkyl, alkoxy;

$R^6$ and $R^7$ are independently chosen from alkyl and aryl.

Examples of the ligands of the present invention are:

Ligand 1

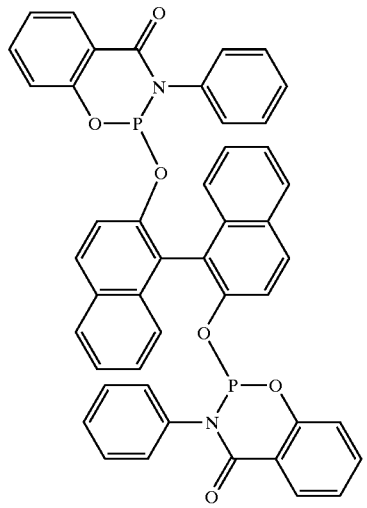

Ligand 2

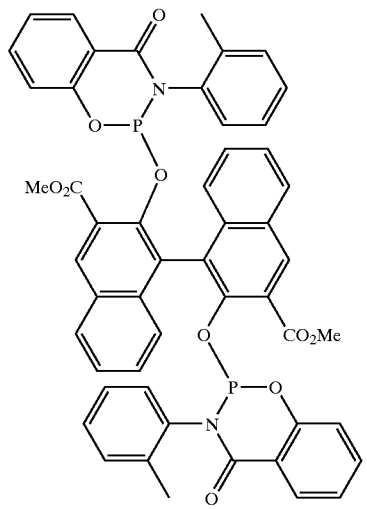

Ligand 3

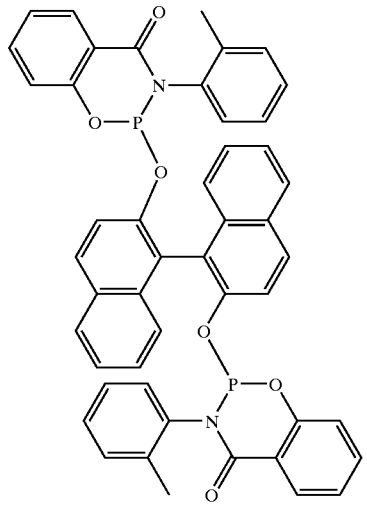

-continued
Ligand 4
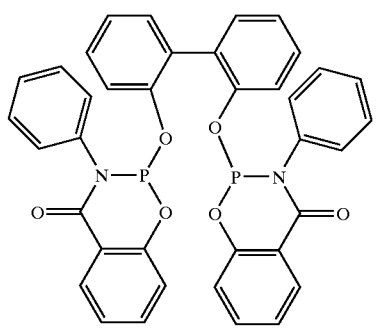
Ligand 5
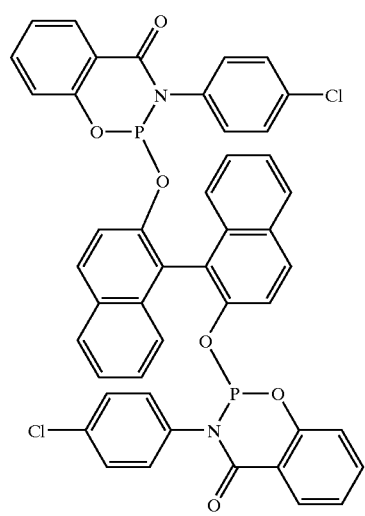
Ligand 6
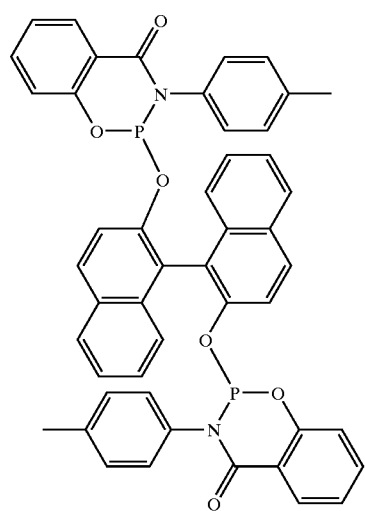
-continued
Ligand 7
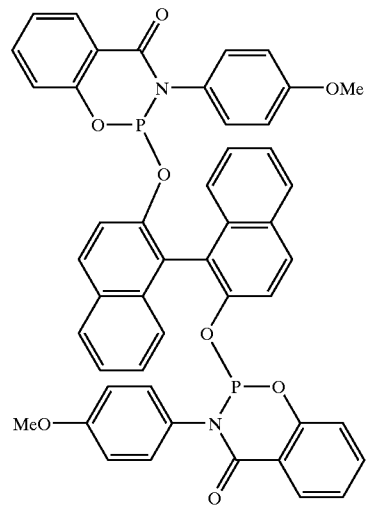
Ligand 8
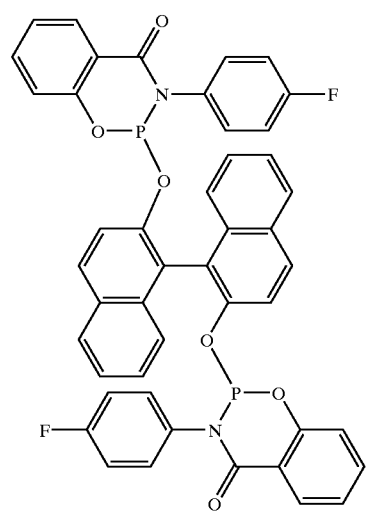
Ligand 9
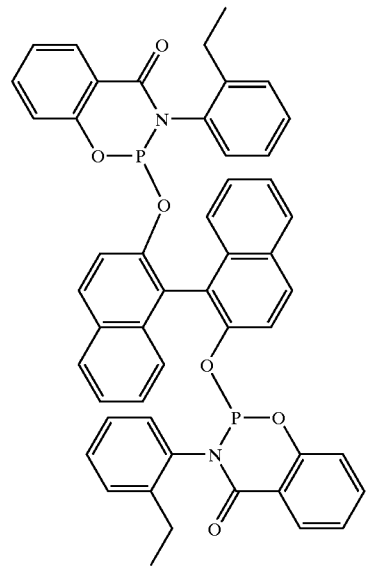

Ligand 10

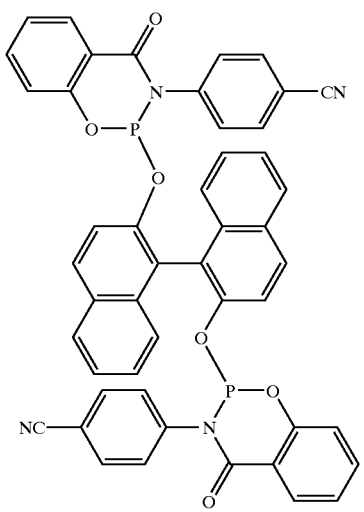

Ligand 11

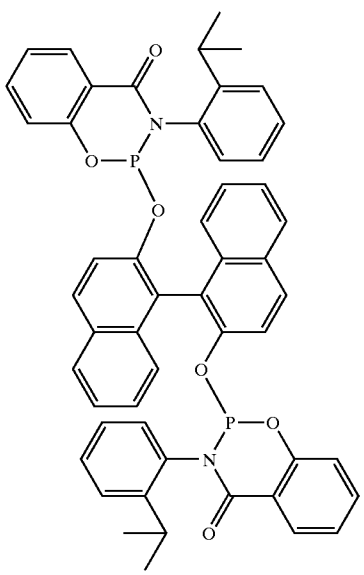

Ligand 12

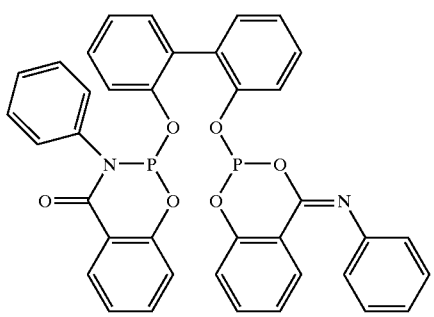

Ligand 13

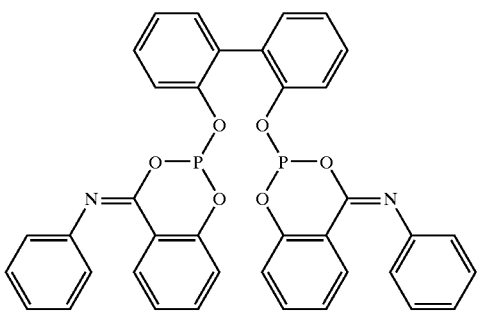

Salicylanilides may be prepared by the amidation of phenyl salicylates with anilines or by treating salicyl chlorides (often prepared in situ with $SOCl_2$, $PCl_3$, or $POCl_3$ with anilines). Both chemistries can be extended to 1-hydroxy-2-naphthoic or 2-hydroxy-3-naphthoic acid derivatives to prepare the naphthyl analogs.

Salicylanilides can react with phosphorus trichloride ($PCl_3$) to yield compounds where the salicylanilide acts as a dianionic chelate to the phosphorus atom. Two possible product structures (A and B) are shown below that differ in the salicylanilide atoms linked to phosphorus (linkage isomers). For the examples provided below, a single $^{31}P$ NMR peak in the region of 140 ppm was observed.

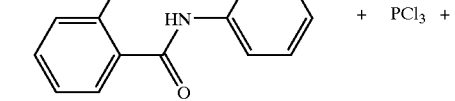

$\xrightarrow[-2\ Base\ HCl]{Base}$

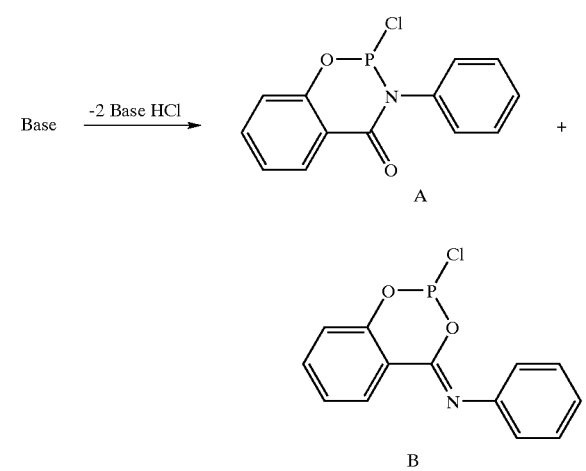

We have found that in the presence of a base, like triethylamine, the product A, B, or a combination of A and B, reacts with organic bridging groups (unsubstituted or substituted 2,2'-biphenol or 1,1'-bi-2-naphthols) to form a single or mixture of ligands that may be used in the process of the present invention. Dependent upon the bridging and salicylanilide groups, the 140 ppm $^{31}P$ NMR peak for A or B is converted to a single or multiple peaks in the 109–121 ppm region. For the ligand product mixtures, the NMR analysis distinguishes phosphorus atoms in different chemical environments.

The catalyst system of the present invention can be prepared by combining a suitable Group VIII metal or a Group VIII metal compound with a phosphorus-containing ligand, optionally in a suitable solvent, in accordance with methods known for forming complexes.

Examples of suitable Group VIII metals are ruthenium, rhodium, and iridium. Examples of suitable Group VIII metal compounds are, for example, $Ru_3(CO)_{12}$, $Ru(NO_3)_3$, $RuCl_3(Ph_3P)_3$, $Ru(acac)_3$, $Ir_4(CO)_{12}$, $IrSO_4$, $RhCl_3$, $Rh(NO_3)_3$, $Rh(OAc)_3$, $Rh_2O_3$, $Rh(acac)(CO)_2$, $[Rh(OAc)(COD)]_2$, $Rh_4(CO)_{12}$, $Rh_6(CO)_{16}$, $RhH(CO)(Ph_3P)_3$, $[Rh(OAc)(CO)_2]_2$, and $[RhCl(COD)]_2$ (wherein "acac" is an acetylacetonate group; "Ac" is an acetyl group; "COD" is 1,5-cyclo-octadiene; and "Ph" is a phenyl group). However, it should be noted that the Group VIII metal compounds are not necessarily limited to the above listed compounds. The source for the Group VIII metal is preferably rhodium. The source for suitable Group VIII metal compounds include, but are not limited to, hydrides, halides, organic acid salts, acetylacetonates, inorganic acid salts, oxides, carbonyl compounds and amine compounds of Group VIII metals.

The unsaturated organic compound that is used in the present invention must have at least one "C=C" bond in the molecule, and preferably, 2 to 20 carbon atoms. Suitable ethylenically unsaturated organic compounds for use in the present invention include, but are not limited to, linear terminal olefinic hydrocarbons. Some examples of these are ethylene, propylene, 1-butene, 1-pentene, 1-hexene, 1-octene, 1-nonene, 1-decene, 1-tetradecene, 1-hexadecene, 1-octadecene, 1-eicosene and 1-dodecene; branched terminal olefinic hydrocarbons, for example isobutene and 2-methyl-1-butene; linear internal olefinic hydrocarbons, for example cis- and trans-2-butene, cis- and trans-2-hexene, cis- and trans-3-hexene, cis- and trans-2-octene and cis- and trans-3-octene; branched internal olefinic hydrocarbons, for example 2,3-dimethyl-2-butene, 2-methyl-2-butene and 2-methyl-2-pentene; terminal olefinic hydrocarbon-internal olefinic hydrocarbon mixtures, for example octenes prepared by dimerization of butenes, olefin oligomer isomer mixture of from dimer to tetramer of lower olefins including propylene, n-butene, isobutene or the like; and cycloaliphatic olefinic hydrocarbons for example cyclopentene, cyclohexene, 1-methylcyclohexene, cyclooctene and limonene. Butadiene, methallyl acetate, 3-pentenoic acid, and unsaturated organic compounds having 6 to 20 carbon atoms, such as alkyl 3-pentenoates, are also useful in the present invention.

Suitable olefinic compounds include those substituted with an unsaturated hydrocarbon group including compounds containing an aromatic substituent such as styrene, α-methylstyrene and allylbenzene; and diene compounds such as butadiene, 1,5-hexadiene, 1,7-octadiene and norbornadiene. It has been found that with the process according to this invention it is possible to prepare 3-pentenal from butadiene in high yield.

The unsaturated organic compound can be substituted with one or more functional groups containing a heteroatom, such as oxygen, sulfur, nitrogen or phosphorus. These heteroatom substituted unsaturated organic compounds include, but are not limited to, vinyl methyl ether, methyl oleate, oleyl alcohol, allyl alcohol, methallyl alcohol, methallyl acetate, methyl 2-pentenoate, methyl 3-pentenoate, methyl 4-pentenoate, 3-pentenoic acid, 4-pentenoic acid, 1,7-octadiene, 7-octen-1-al, acrylonitrile, acrylic acid esters, methylacrylate, methacrylic acid esters, and methylmethacrylate.

A special class of internally unsaturated organic compounds is 3-pentenoic acid and C1–C6 alkyl 3-pentenoate ester compounds. Terminal aldehyde compounds prepared by the disclosed process starting from these compounds can be used advantageously in the preparation of γ-caprolactam or adipic acid, which are precursors for respectively Nylon-6 and Nylon-6,6. Examples of C1–C6 alkyl 3-pentenoates are methyl-, ethyl-, propyl-, isopropyl-, tert-butyl-, pentyl and cyclohexyl 3-pentenoate. Methyl and ethyl 3-pentenoate esters are preferred because they are more readily available.

The 3-pentenoic acid and C1–C6 alkyl 3-pentenoate ester compounds may be present in mixtures containing, respectively, 2- and 4-pentenoic acid; and C1–C6 alkyl 2- and 4-pentenoate ester compounds. Since these compounds react in a similar fashion as the 3-isomer to the desired terminal aldehyde, a mixture of isomers can be directly used in the process according to the invention.

The hydroformylation process is carried out under conditions that will be dependent on the particular starting unsaturated organic compound. The temperature for the reaction can be from about room temperature to about 200° C., preferably from about 50° C. to about 150° C. The pressure may vary from normal pressure to 20 MPa, preferably from 0.15 to 10 Mpa, and more preferably from 0.2 to 5 MPa. The pressure is, as a rule, equal to the combined hydrogen and carbon monoxide partial pressure. Extra inert gases may, however, be present. The molar ratio of hydrogen:carbon monoxide is generally between 10:1 and 1:10, and preferably between 6:1 and 1:2.

In general, the concentration of Group VIII metal or Group VIII metal compound in the reaction medium is between 10 and 10,000 ppm, and more preferably between 100–1000 ppm, calculated as free metal.

The molar ratio of multidentate phosphorus ligand to Group VIII metal or Group VIII metal compound is from about 0.5 to 100, and preferably from 1 to 10 (mol ligand/mol metal).

The solvent may be a mixture of reactants from the hydroformylation itself, such as the starting unsaturated compound, the aldehyde product and/or by-products. Optionally, a solvent that is not a mixture of the reactants may be used. Solvents that are suitable for use in the present invention include saturated hydrocarbons (for example kerosene, mineral oil, or cyclohexane), ethers (for example diphenyl ether or tetrahydrofuran), ketones (for example acetone, cyclohexanone), nitrites (for example acetonitrile, adiponitrile or benzonitrile), aromatics (for example toluene, benzene or xylene), esters (for example methyl valerate, caprolactone), Texanol® (available from Union Carbide), or dimethylformamide.

Various embodiments of the present invention are exemplified in the following non-limiting examples.

EXAMPLES

Example 1

Methyl 3-Pentenoate Hydroformylation with Rhodium and Ligand Mixture 1 Derived from Salicylanilide, $PCl_3$ and Binaphthol (a) Preparation of Ligand Mixture 1

In a nitrogen-filled drybox, salicylanilide (4.26 gm, 20 mmol), $PCl_3$ (2.74 gm, 20 mmol), and dry triethylamine (4.04 gm, 40 mmol) were combined in a flask containing dry tetrahydrofuran (50 mL). After stirring overnight, a $^{31}P$ NMR analysis showed a single peak at 140 ppm. Dry triethylamine (2.02 gm, 20 mmol) and 1,1'-bi-2-naphthol (2.86 gm, 10 mmol) were added to the tetrahydrofuran solution then the mixture was stirred overnight. Another $^{31}P$ NMR analysis indicated complete conversion to new compounds with several peaks between 117–118.5 ppm. The tetrahydrofuran was evaporated then dry diethyl ether (30 mL) was added to dissolve the desired product. After separating the ammonium salts by filtration, the ether filtrate was evaporated to yield a residue. Crystallization from $CH_2Cl_2$/hexanes gave a yellow solid. FAB (Fast Atom Bombardment) MS: m/e=769 (M$^+$, calc. $C_{46}H_{30}O_6N_2P_2$ 768.7).

(b) Methyl 3-Pentenoate Hydroformylation with Rhodium and Ligand Mixture from Example 1a;

A 25 mL glass-lined pressure vessel was charged with 5 mL of a solution containing 11.4 gm (100 mmol) methyl 3-pentenoate, 0.068 gm (0.2 mmol) of dicarbonyl(2,2,6,6-tetramethyl-3,5-heptanedionato)rhodium, 0.78 g (1.0 mmol) of the mixture from Example 1a and 1.00 gm of tetradecane (internal GC standard) in 100 mL toluene. The pressure vessel was freed from air by purging first with nitrogen (twice) and then with 1:1 $CO/H_2$ (twice). The vessel was then pressurized to 75 psi CO and heated to 100° C. with agitation for 2 hours. The heat was shut off and the pressure vessel was allowed to cool to room temperature. The excess gases were vented and the products were analyzed by GC. Methyl 3-pentenoate conversion (% methyl 3-pentenoate and methyl 4-pentenoate reacted): 80.3%; Linearity [100× methyl 5-formylvalerate/(methyl 5-formylvalerate+branched formylvalerates)]: 84.8%; Selectivity (100×methyl 5-formylvalerate/All Products]: 73.3%.

Example 2

Methyl 3-Pentenoate Hydroformylation with Rhodium and Ligand Mixture 2 Derived from 2'-Methyl-salicylanilide, $PCl_3$, and Dimethyl 2,2'-Dihydroxy-1,1'-Binaphthalene-3,3'-Dicarboxylate (a) Preparation of Ligand Mixture 2

Phenol was distilled from a boiling mixture of phenyl salicylate (42.8 gm, 0.20 mol), 2-toluidine (26.7 gm, 0.25 mol), and 1,2,4-trichlorobenzene (41 mL) as described in the literature procedure (Organic Syntheses, Coll. Vol. 3, 765). The cooled product mixture was transferred to an 250 mL Erlenmeyer flask and boiled with hexanes (75 mL) for 30 minutes. The solid product was isolated from the hot mixture by vacuum filtration. The solid was washed with more hexanes until the filtrate was colorless. Drying gave the pure 2'-methyl-salicylanilide (41 gm, 90%) as an off-white solid.

In a nitrogen-filled drybox, the 2'-methyl-salicylanilide (2.27 gm, 10 mmol), $PCl_3$ (1.37 gm, 10 mmol), and dry triethylamine (2.02 gm, 20 mmol) were combined in a flask containing dry tetrahydrofuran (50 mL). After stirring overnight, a $^{31}P$ NMR analysis showed a single peak at 141 ppm. Dry triethylamine (1.01 gm, 10 mmol) and dimethyl 2,2'-dihydroxy-1,1'-binaphthalene-3,3'-dicarboxylate (2.01 gm, 5 mmol) were added to the tetrahydrofuran solution then the mixture was stirred overnight. Another $^{31}P$ NMR analysis indicated complete conversion to new compounds with several peaks between 116–119 ppm. The tetrahydrofuran was evaporated then dry diethyl ether (30 mL) was added to dissolve the desired product. After separating the ammonium salts by filtration, the ether filtrate was evaporated to yield a residue which was used for catalysis.

(b) Methyl 3-Pentenoate Hydroformylation with Rhodium and Ligand Mixture Derived from Example 2a The experiment in Example 1b was repeated except that mixture derived from Example 1a was replaced with the mixture derived from Example 2a (45.6 mg/5 mL). GC analysis indicated 80.6% methyl 3-pentenoate conversion with a selectivity to methyl 5-formylvalerate of 71.2% and a linearity of 88.7%.

Example 3

Methyl 3-Pentenoate Hydroformylation with Rhodium and Ligand Mixture 3 Derived from 2'-Methyl-salicylanilide, $PCl_3$, and Binaphthol (a) Preparation of Ligand Mixture 3

2-Methyl-salicylanilide was prepared by condensing phenyl salicylate with 2-toluidine then purified as described in Example 2a. The ligand mixture was then prepared from 2-methyl-salicylanilide and 1,1'-bi-2-naphthol using the procedure described in Example 2a. $^{31}P$ NMR (121.77 MHz): several peaks between 109–120 ppm.

(b) Methyl 3-Pentenoate Hydroformylation with Rhodium and Ligand Mixture Prepared in Example 3a The experiment in Example 1b was repeated except that mixture prepared in Example 1a was replaced with the mixture prepared in Example 3a (45.6 mg/5 mL). The GC result is given in Table 1.

Example 4

Methyl 3-Pentenoate Hydroformylation with Rhodium and Ligand Mixture 4 Derived from Salicylanilide, $PCl_3$ and Biphenol (a) Preparation of Ligand Mixture 4

The biphenol analog of the ligand mixture prepared in Example 1a was prepared from salicylanilide and 2,2'-biphenol as described in Example 1a. $^{31}P$ NMR (121.77 MHz): 112 ppm along with small peaks at 138 ppm and 113 ppm.

(b) Methyl 3-Pentenoate Hydroformylation with Rhodium and the Ligand Mixture Prepared in Example 4a The experiment in Example 1b was repeated except that mixture prepared from Example 1a was replaced with the mixture prepared in Example 4a (33.4 mg/5 mL). The GC result is given in Table 1.

Example 5

Methyl 3-Pentenoate Hydroformylation with Rhodium and Ligand Mixture 5 Derived from 4'-Chloro-Salicylanilide, $PCl_3$ and Binaphthol (a) Preparation of Ligand Mixture 5

The 4'-chloro-salicylanilide was prepared by condensing phenyl salicylate with 4-chloroaniline then purified as described in Example 2a.

Under a dry nitrogen atmosphere, the 4'-chloro-salicylanilide (2.79 gm, 11 mmol), $PCl_3$ (4.6 gm, 34 mmol), and dry triethylamine (4.55 gm, 45 mmol) were combined in a flask containing dry toluene (40 mL) then refluxed for 4 hours. In the drybox, the ammonium salts were separated by filtration then washed with dry toluene (2×10 mL). The combined filtrates were evaporated. A $^{31}P$ NMR analysis showed a single peak at 139.4 ppm.

1,1'-Bi-2-naphthol (1.43 gm, 5 mmol) and the 4'-chloro salicylanilide/$PCl_3$ reaction product (2.95 gm, 10 mmol) were dissolved in dry diethyl ether (50 mL) then treated dropwise with dry triethylamine (1.01 gm, 10 mmol). After stirring overnight, another $^{31}P$ NMR analysis indicated complete conversion to a new compound with a 117.1 ppm chemical shift. After separating the ammonium salts by filtration, the ether filtrate was evaporated to yield an orange powder.

(b) Methyl 3-Pentenoate Hydroformylation with Rhodium and the Ligand Mixture 5 Prepared from Example 5a The experiment in Example 1b was repeated except that mixture prepared in Example 1a was replaced with a mixture prepared from Example 5a (41.9 mg/5 mL). The GC result is given in Table 1.

Example 6

Methyl 3-Pentenoate Hydroformylation with Rhodium and the Ligand Mixture 6 Derived from 4'-Methyl-salicylanilide, $PCl_3$ and Binaphthol (a) Preparation of Ligand Mixture 6

The 4'-methyl-salicylanilide was prepared by condensing phenyl salicylate with 4-toluidine then purified as described in Example 2a. A ligand mixture was then prepared from 4'-methyl-salicylanilide and binaphthol using the procedure described in Example 5a. $^{31}P$ NMR (121.77 MHz): several peaks between 117.1–117.8 ppm.

(b) Methyl 3-Pentenoate Hydroformylation with Rhodium and the Ligand Mixture Prepared from Example 6a The experiment in Example 1b was repeated except that mixture prepared in Example 1a was replaced with a mixture prepared from Example 6a (39.8 mg/5 mL). The GC result is given in Table 1.

Example 7

Methyl 3-Pentenoate Hydroformylation with Rhodium and the Ligand Mixture 7 Derived from 4'-Methoxy-Salicylanilide, $PCl_3$, Binaphthol (a) Preparation of the Ligand Mixture 7

The 4'-methoxy-salicylanilide was prepared by condensing phenyl salicylate with 4-aminoanisole then purified as described in Example 2a. The mixture of ligands was then prepared from 4'-methoxy-salicylanilide and 1,1'-bi-2-naphthol using the procedure described in Example 5a. $^{31}P$ NMR (121.77 MHz): several peaks between 116–118 ppm.

(b) Methyl 3-Pentenoate Hydroformylation with Rhodium and the Ligand Mixture Prepared from Example 7a The experiment in Example 1b was repeated except that mixture prepared in Example 1a was replaced with the mixture prepared from Example 7a (41.4 mg/5 mL). The GC result is given in Table 1.

Example 8

Methyl 3-Pentenoate Hydroformylation with Rhodium and Mixture 8 Derived from 4'-Fluoro-Salicylanilide, $PCl_3$ and Binaphthol (a) Preparation of Ligand Mixture 8

The 4'-fluoro-salicylanilide was prepared by condensing phenyl salicylate with 4-fluoroaniline then purified as described in Example 2a. The ligand mixture was then prepared from 4'-fluoro-salicylanilide and 1,1'-bi-2-naphthol using the procedure described in Example 5a. $^{31}P$ NMR (121.77 MHz): several peaks between 117.1–117.7 ppm.

(b) Methyl 3-Pentenoate Hydroformylation with Rhodium and the Ligand Mixture Prepared from Example 9a The experiment in Example 1b was repeated except that the mixture prepared from Example 1a was replaced with the mixture prepared in Example 8a (40.2 mg/5 mL). The GC result is given in Table 1.

Example 9

Methyl 3-Pentenoate Hydroformylation with Rhodium and Ligand Mixture 9 Derived from 2'-Ethyl-Salicylanilide, $PCl_3$ and Binaphthol (a) Preparation of Ligand Mixture 9

The 2'-ethyl-salicylanilide was prepared by condensing phenyl salicylate with 2-ethylaniline then purified as described in Example 2a. The ligand mixture was then prepared from 2'-ethyl-salicylanilide and 1,1'-bi-2-naphthol using the procedure described in Example 2a. $^{31}P$ NMR (121.77 MHz): several peaks between 117.1–118.8 ppm.

(b) Methyl 3-Pentenoate Hydroformylation with Rhodium and Mixture Prepared from Example 9a The experiment in Example 1b was repeated except that mixture prepared in Example 1b was replaced with the mixture prepared from Example 9a (41.2 mg/5 mL). The GC result is given in Table 1.

Example 10

Methyl 3-Pentenoate Hydroformylation with Rhodium and Ligand Mixture 10 Derived from 4'-Cyano-Salicylanilide, $PCl_3$ and Binaphthol (a) Preparation of Ligand Mixture 10

The 4'-cyano-salicylanilide was prepared by condensing phenyl salicylate with 4-amino-benzonitrile then purified as described in Example 2a. The ligand mixture was then prepared from 4'-cyano-salicylanilide and 1,1'-bi-2-naphthol using the procedure described in Example 5a. $^{31}P$ NMR (121.77 MHz): several peaks between 116.4–117.7 ppm.

(b) Methyl 3-Pentenoate Hydroformylation with Rhodium and the Ligand Mixture Prepared in Example 10a The experiment in Example 1b was repeated except that the mixture prepared in Example 1a was replaced with an equivalent amount of the mixture prepared in Example 10a (40.9 mg/5 mL). The GC result is given in Table 1.

Example 11

Methyl 3-Pentenoate Hydroformylation with Rhodium and the Ligand Mixture 11 Derived from 2'-Isopropyl-Salicylanilide, $PCl_3$, and Binaphthol (a) Preparation of the Ligand Mixture 11

The 2'-isopropyl-salicylanilide was prepared by condensing phenyl salicylate with 2-isopropylaniline then purified as described in Example 2a. The ligand mixture was then prepared from 2'-isopropyl-salicylanilide and binaphthol using the procedure described in Example 2a. $^{31}P$ NMR (121.77 MHz): several peaks between 117.1–120.9 ppm.

(b) Methyl 3-Pentenoate Hydroformylation With Rhodium and Ligand Mixture Prepared in Example 11a The experiment in Example 1b was repeated except that mixture prepared in Example 1a was replaced with the mixture derived in Example 11a (42.6 mg/5 mL). The GC result is given in Table 1.

TABLE 1

Methyl 3-Pentenoate Hydroformylation Results with Catalysts Derived from Rhodium and Ligand Mixtures Prepared from Examples 3a–11a

| Example | Ligand | Methyl 3-Pentenoate Conversion (%) | C6 Aldehyde Linearity (%) | C6 Linear Aldehyde Selectivity (%) |
|---|---|---|---|---|
| 3 | 3 | 33.0 | 91.0 | 68.5 |
| 4 | 4 | 75.9 | 77.5 | 67.2 |
| 5 | 5 | 29.8 | 83.4 | 65.5 |
| 6 | 6 | 58.8 | 85.4 | 64.4 |
| 7 | 7 | 18.8 | 79.0 | 59.2 |
| 8 | 8 | 62.3 | 80.2 | 58.0 |
| 9 | 9 | 70.4 | 80.8 | 57.3 |
| 10 | 10 | 16.5 | 85.4 | 56.2 |
| 11 | 11 | 85.4 | 67.9 | 50.7 |

Examples 12–13

1,3-Butadiene Hydroformylation with Rhodium and Ligand Mixtures Prepared in Examples 5a and 6a The experiment in Example 1b was repeated except that the methyl 3-pentenoate was replaced by an equivalent amount of 1,3-butadiene, the solvent was tetrahydrofuran, the total $CO/H_2$ pressure was 1000 psi (6.8 Mpa), the temperature was 90° C., and ligands prepared in Examples 5a and 6a, respectively, were utilized. Analysis of the products after 2 hours reaction time showed a mixture of unreacted 1,3-butadiene, pentanal (reduction product), pentenals (primarily trans-3-pentenal) and C6 dialdehydes (primarily 1,4-butanedial). The results are summarized in Table 2 (moles formed per 100 moles butadiene charged).

TABLE 2

1,3-Butadiene Hydroformylation with Rhodium and Ligand Mixtures from Examples 5a or 6b.

| Examples | Ligand Number | 1,3-Butadiene Unreacted (mol) | Pentanal (mol) | 3-Pentenals (mol) | C6 Dialdehydes (mol) |
|---|---|---|---|---|---|
| 12 | 5 | 14.4 | 1.1 | 57.7 | 1.7 |
| 13 | 6 | 46.4 | 0.0 | 16.6 | 0.0 |

Examples 14–15

Methallyl Acetate (2-Methyl-2-Propene-1-Acetate) Hydroformylation with Rhodium and Ligand Mixture Prepared in Example 11a The experiment in Example 11b was repeated except that the methyl 3-pentenoate was replaced by an equivalent amount of methallyl acetate, the temperature was 90° C., the $CO/H_2$ pressure at temperature (90° C.) was varied and the reaction was allowed to run for 4 hours. Analysis of the product by GC showed only the terminal aldehyde, 4-acetoxy-3-methylbutanal (4Ac3MB), and the reduced product, isobutyl acetate (i-BuOAc). The results are summarized in Table 3.

TABLE 3

Hydroformylation of Methallyl Acetate with Rhodium and Ligand Mixture Prepared in Example 11a.

| Example | $CO/H_2$ Pressure (psi) | Methallyl Acetate Conv. (%) | 4Ac3MB Select. (%) | i-BuAc Select. (%) | Aldehyde Linearity (%) |
|---|---|---|---|---|---|
| 14 | 75 | 72.1 | 69.7 | 7.4 | 100 |
| 15 | 150 | 74.2 | 72.2 | 8.0 | 100 |

What is claimed is:

1. A hydroformylation process for preparing an organic aldehyde compound from an unsaturated organic compound, said method comprising: contacting an unsaturated organic compound with carbon monoxide, hydrogen gas, and a catalyst system, said catalyst system comprising a Group VIII metal, and at least one or a combination of at least two bidentate organic ligands having two trivalent phosphorus atoms, said ligand selected from the group consisting of structure I, II, III, IV, V, and VI:

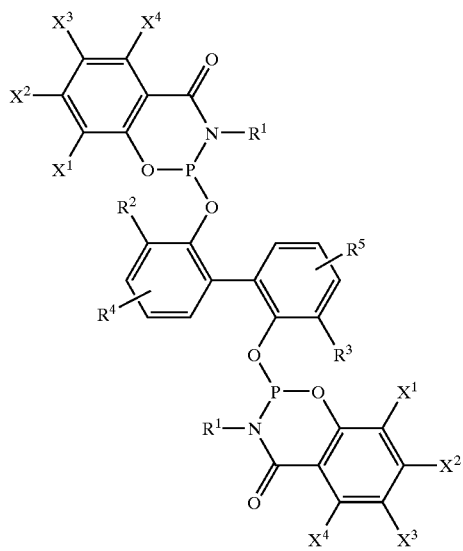

Structure I

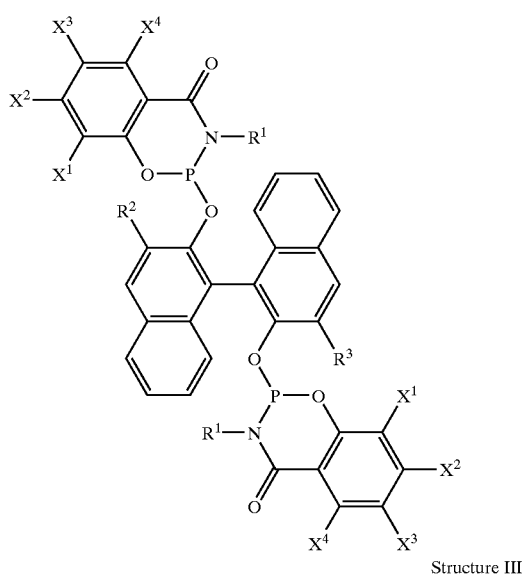

Structure II

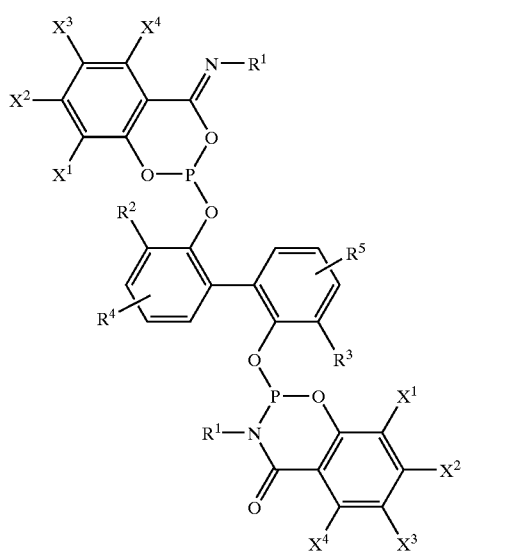

Structure III

-continued

Structure IV

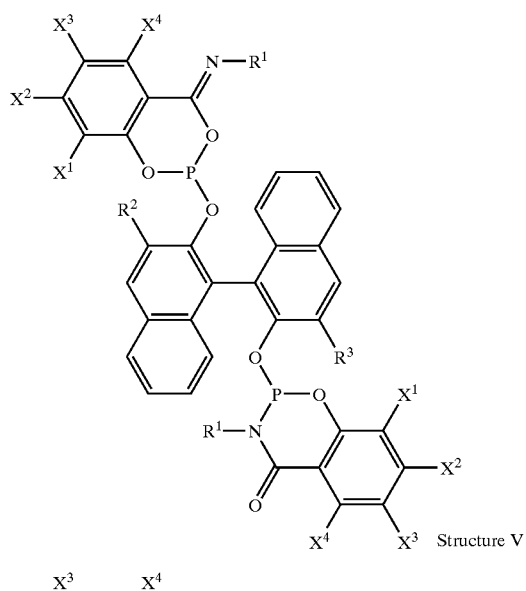

Structure V

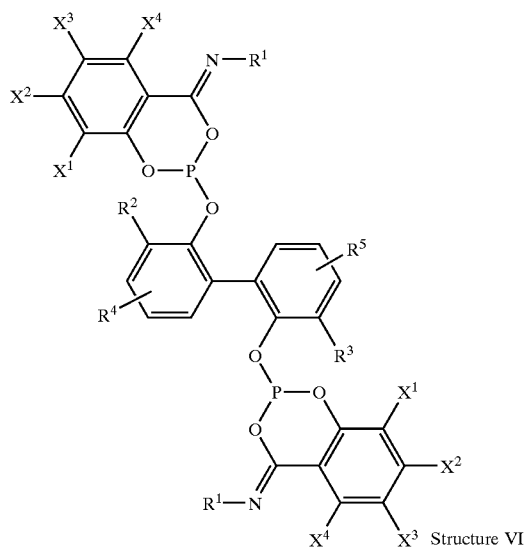

Structure VI

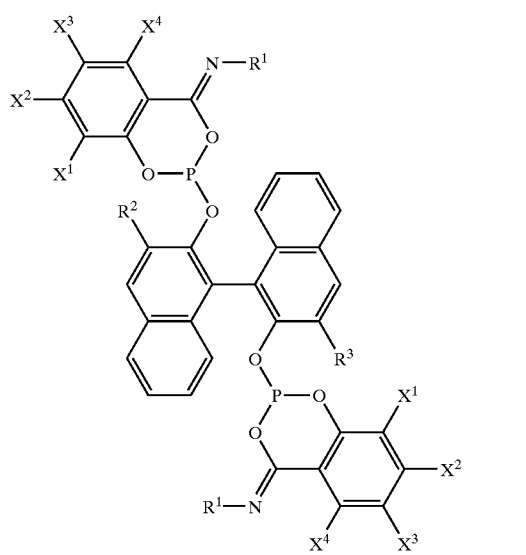

where $X^1$–$X^4$ are C1–C6 alkyl, alkoxy, aryloxy, $NR^6R^7$, Cl, F, or $CF_3$;

$R^1$ is independently selected from the group consisting of substituted aryl, phenyl, or fused aromatic ring systems;

$R^2$ and $R^3$ are independently selected from the group consisting of hydrogen, alkyl, aryl, triarylsilyl, trialkylsilyl, carboalkoxy, carboaryloxy, aryloxy, alkoxy, alkylcarbonyl, arylcarbonyl, or nitrile;

$R^4$ and $R^5$ are independently selected from the group consisting of hydrogen, alkyl, alkoxy;

$R^6$ and $R^7$ are independently chosen from alkyl and aryl.

2. A process according to claim 1 wherein the Group VIII metal is ruthenium, rhodium, or iridium.

3. A process according to claim 2 wherein Group VIII metal is provided in the form of $Ru_3(CO)_{12}$, $Ru(NO_3)_3$, $RuCl_3(Ph_3P)_3$, $Ru(acac)_3$, $Ir_4(CO)_{12}$, $IrSO_4$, $RhCl_3$, $Rh(NO_3)_3$, $Rh(OAC)_3$, $Rh_2O_3$, $Rh(acac)(CO)_2$, $[Rh(OAc)(COD)]_2$, $Rh_4(CO)_{12}$, $Rh_6(CO)_{16}$, $RhH(CO)(Ph_3P)_3$, $[Rh(OAc)(CO)_2]_2$, or $[RhCl(COD)]_2$.

4. A process according to claim 2 wherein the catalyst system comprises rhodium.

5. A process according to claim 1 wherein the unsaturated compound is selected from the group consisting of ethylene, propylene, 1-butene, 1-pentene, 1-hexene, 1-octene, 1-nonene, 1-decene, 1-tetradecene, 1-hexadecene, 1-octadecene, 1-eicosene and 1-dodecene, isobutene, 2-methyl-1-butene, 2-butene, 2-hexene, 3-hexene, 2-octene, 3-octene; 2,3-dimethyl-2-butene, 2-methyl-2-butene, 2-methyl-2-pentene, octene, propylene, n-butene, isobutene, cyclopentene, cyclohexene, 1-methylcyclohexene, cyclooctene, limonene, butadiene, methallyl acetate, 3-pentenoic acid, and alkyl 3-pentenoates.

6. A process according to claim 1 wherein the unsaturated organic compound is selected from the group consisting of styrene, α-methylstyrene, allylbenzene, hexadiene, octadiene and norbornadiene.

7. A process according to claim 1 wherein the unsaturated organic compound is selected from the group consisting of vinyl methyl ether, methyl oleate, oleyl alcohol, allyl alcohol, methallyl alcohol, methallyl acetate, methyl 2-pentenoate, methyl 3-pentenoate, methyl 4-pentenoate, 3-pentenoic acid, 4-pentenoic acid, 1,7-octadiene, 7-octen-1-al, acrylonitrile, acrylic acid esters, methylacrylate, methacrylic acid esters, and methylmethacrylate.

8. A process according to claim 1 wherein the unsaturated compound is 3-pentenoic acid or a C1–C6 alkyl 3-pentenoate ester compound.

9. A bidentate ligand having two trivalent phosphorus atoms represented by structure I, II, III, IV, V, or VI:

Structure I
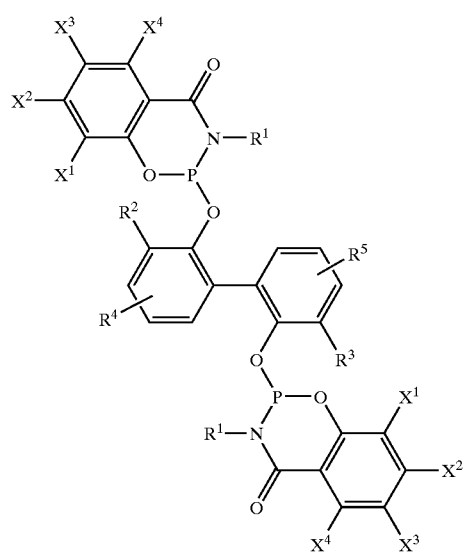
Structure II
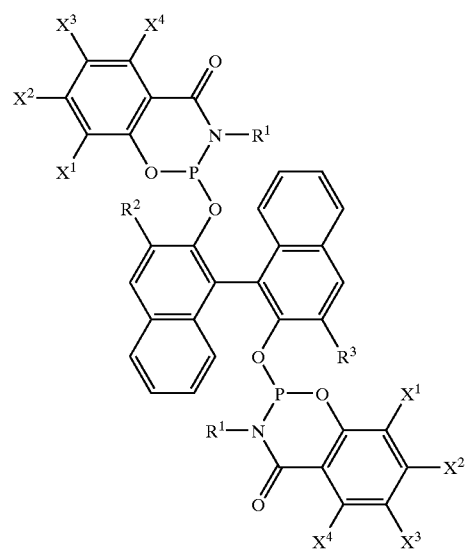
Structure III
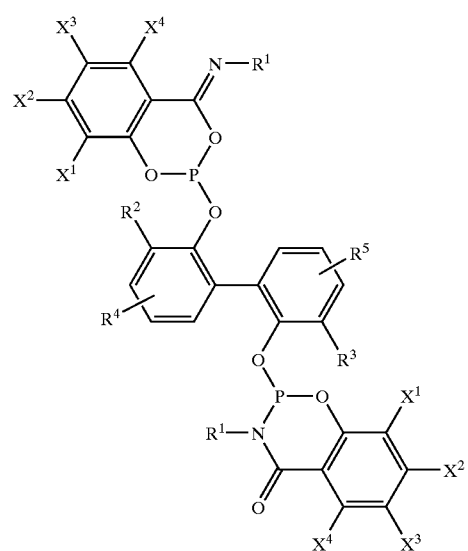
Structure IV
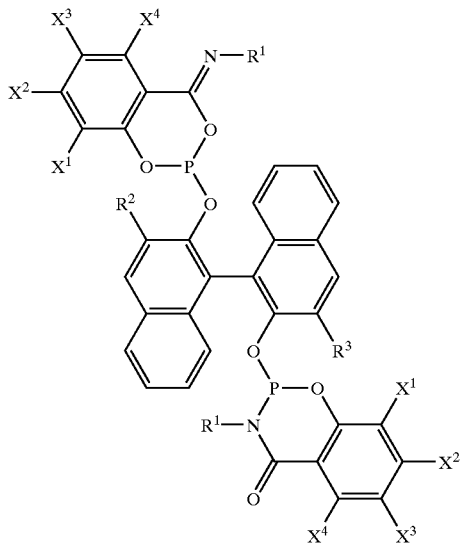
Structure V
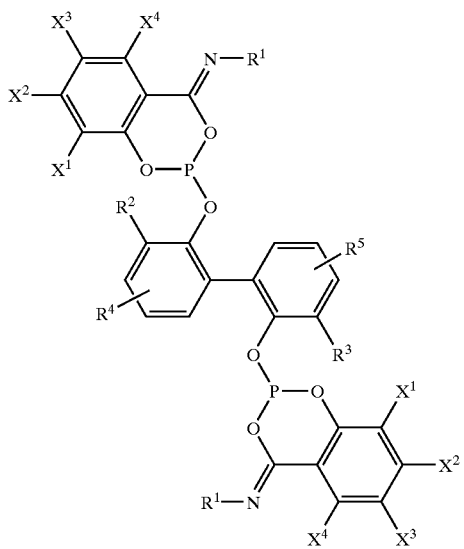
Structure VI
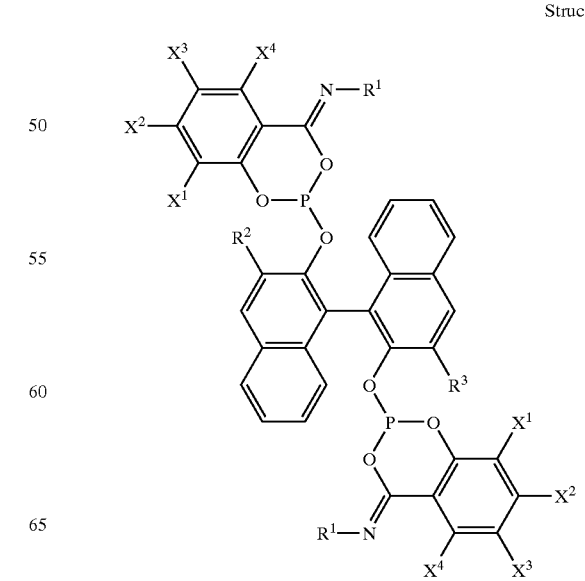

where $X^1$–$X^4$ are C1–C6 alkyl, alkoxy, aryloxy, $NR^6R^7$, Cl, F, or $CF_3$;

$R^1$ is independently selected from the group consisting of substituted aryl, phenyl, or fused aromatic ring systems;

$R^2$ and $R^3$ are independently selected from the group consisting of hydrogen, alkyl, aryl, triarylsilyl, trialkylsilyl, carboalkoxy, carboaryloxy, aryloxy, alkoxy, alkylcarbonyl, arylcarbonyl, or nitrile;

$R^4$ and $R^5$ are independently selected from the group consisting of hydrogen, alkyl, alkoxy;

$R^6$ and $R^7$ are independently chosen from alkyl and aryl.

10. A bidentate ligand according to claim 9 wherein $R^2$ and $R^3$ each are carboalkoxy groups in which R is C1–C8 alkyl.

11. A composition of matter comprising a combination of at least two ligands according to claim 9.

* * * * *